United States Patent [19]

Koshugi

[11] 4,376,199

[45] Mar. 8, 1983

[54] SHAPED MATERIAL OF CHITIN DERIVATIVES

[75] Inventor: Junichi Koshugi, Tokyo, Japan

[73] Assignee: Kureha Kagaku Kogyo Kabushiki Kaisha, Japan

[21] Appl. No.: 198,193

[22] Filed: Oct. 17, 1980

[30] Foreign Application Priority Data

Oct. 24, 1979 [JP] Japan .................................. 54-137337

[51] Int. Cl.³ .............................................. C08B 37/08
[52] U.S. Cl. ....................................... 536/20; 424/180
[58] Field of Search ........................................... 536/20

[56] References Cited

U.S. PATENT DOCUMENTS

| | | | |
|---|---|---|---|
| 2,040,879 | 5/1936 | Rigby | 536/20 |
| 3,879,377 | 4/1975 | Austin | 536/20 |
| 4,029,727 | 6/1977 | Austin et al. | 536/20 |
| 4,111,810 | 9/1978 | Arai et al. | 210/23 |

FOREIGN PATENT DOCUMENTS

| | | | |
|---|---|---|---|
| 894993 | of 1949 | Fed. Rep. of Germany | 536/21 |
| 46-39322 | 11/1971 | Japan | 536/20 |

*Primary Examiner*—Johnnie R. Brown
*Attorney, Agent, or Firm*—Wegner & Bretschneider

[57] ABSTRACT

Disclosed herein is a novel shaped material of a derivative of chitin obtainable by partially acylating or partially acid-treating a cross-linked ionic chitin derivatives, which is excellent for use as the material for capsules, as material for dialysis carriers and/or as an ion-exchanger resin.

3 Claims, 1 Drawing Figure

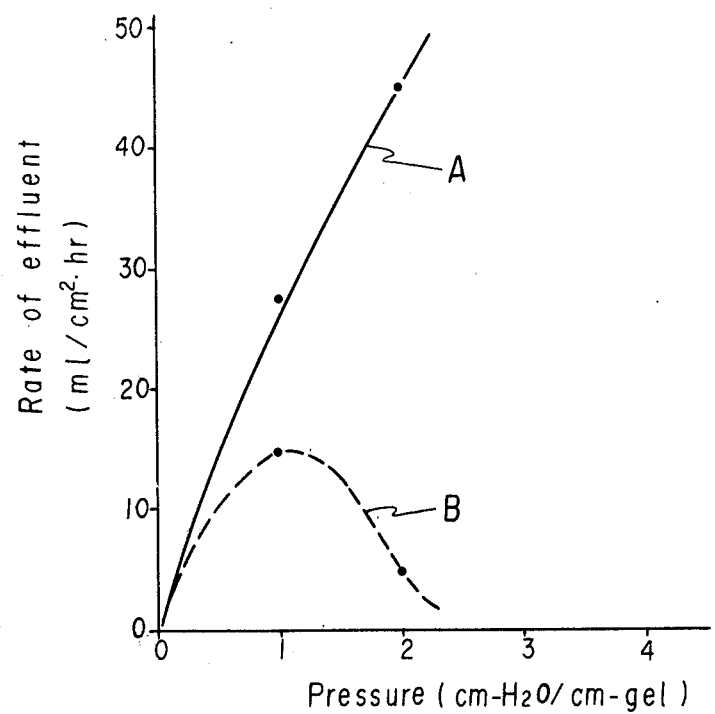

SHAPED MATERIAL OF CHITIN DERIVATIVES

The present invention concerns a novel shaped material, comprising derivatives of chitin, which is excellent as a material for making capsules, as material for dialysis batteries and as material for ion-exchange resens, etc. More precisely, the present invention concerns a shaped material of high mechanical strength prepared by acylating partially a cross-linked ionic chitin derivative having ionizable groups, such as chitosan, de-N-acetylated product of carboxyalkylchitin or a salt thereof, with an organic acid anhydride or an acid.

Fiber-forming polysaccharides occurring in nature are roughtly divided into collagen in higher animals, chitin in arthropods and lower animals and cellulose in higher plants, The frames of the living things are made by the products formed by the sedimentation of apatite, calcium carbonate, lignin, etc. onto the above-mentioned polysaccharides, respectively.

Among them, chitin is a polymeric substance of high molecular weight comprising the 1,4-beta bonding of N-acetyl-D-glucosamine. Its occurrence in nature is favorably comparable to that of cellulose.

However, since chitin is extremely high in crystallinity and inter-molecular bonding between chitin molecules by the amino-acetyl groups is very strong and stable, an economical solvent which favorably dissolves, disperses or swells chitin as an alkali on cellulose has not yet been found.

In these circumstances, the inventor of the present invention formerly offered a method of producing a water-soluble derivative of chitin in Japanese Patent Application No. 161391/78, and a shaped material derived from the above-mentioned water-soluble derivative of chitin in Japanese Patent Application No. 161389/78. Particularly, the invention disclosed in latter Patent Application has made it possible to obtain variously shaped materials having amphoteric ion-exchangability, and is believed to contribute greatly to the effective utilization of chitin resources.

However, in addition to problems concerning the inability of the shaped material to adsorb some kinds of high molecular weight substances through its surface, there is a need for improved mechanical strength of such a material, particularly for certain uses.

As a solution to the above-mentioned problem and to improving the mechanical strength, the inventor of the present invention described an amphoteric ion-exchanger in Japanese Patent Application No. 41812/79, which is obtained by cross-linking chitin, carboxyalkylating the cross-linked chitin, and then de-N-acetylating the thus carboxyalkylated cross-linked chitin. The amphoteric ion-exchanger thus obtained is excellent in adsorbing various substances of high molecular weight.

However, when this amphoteric ion-exchanger is used as an adsorbent in blood dialysis, it adsorbs the high molecular weight substances such as the available proteinic components (which should not be removed) in addition to the toxic substances whose removal is desired. This results in reducing the ability to absorb the substance whose removal is desired. Similar results appear in the case where the material is used as a filler in a chromatographic column, the ability to separate the substances subjected to the chromatography being desired.

The inventor of the present invention has found that the above-mentioned problems of the amphoteric ion-exchanger are caused by the presence of ionic groups on the surface of the ion-exchanger. He has further found that these problems may be solved by acylating or acid-treating the ion-exchanger to substantially eliminate or reduce the ionic groups on the surface.

In view of the above-mentioned recent situation, the present invention has a main object the production of a novel shaped material satisfactory in mechanical strength and in properties of adsorption or separation, etc. by further improving the inventions of the above-mentioned Japanese Patent Applications No. 161389/78 and 41812/79.

The present invention provides a shaped material produced by partially treating a cross-linked ionic chitin derivative with an organic acid anhydride or a mixture thereof with an organic acid to effect an acylation or with an aqueous mineral acidic solution to effect an acid-treatment.

Since the thus produced shaped material of the present invention has its superficial membrane comprising an acylated product and/or a deacetylated product as mentioned hereinafter and has its internal part comprising the above-mentioned crosslinked substance, the shaped material of the present invention is excellent in mechanical strength and so it is very useful as material for capsules, for dialysis and for ion-exchange use, and is applicable in wide range of uses such as material for biofunctions, for collecting heavy metals, base material for fixed enzymes, and for ultrafiltration, etc. In addition, in the course of producing the shaped material of the present invention, the material is very easily handled since the mutual agglomeration caused by the functional groups on the surface of the shaped material does not occur in the step of de-salting.

The present invention will be explained more in detail as follow:

The cross-linked substance of ionic chitin derivative has a main structural unit represented by the formulas Ia and Ib:

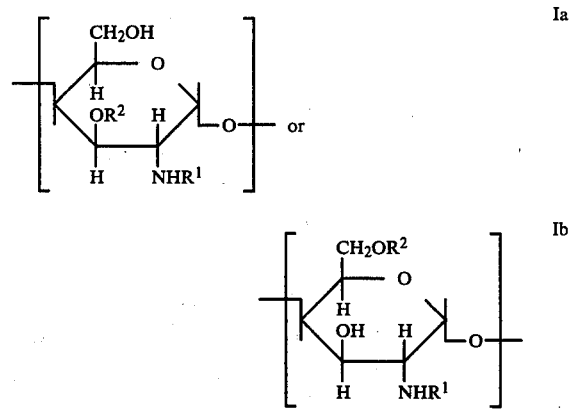

wherein $R^1$ denotes a hydrogen atom, an alkyl group of 1 to 20 carbon atoms, an omega-hydroxyalkyl group of 1 to 20 carbon atoms or an acyl group of 2 to 21 carbon atoms, $R^2$ denotes a hydrogen atom, an alkyl group of 1 to 3 carbon atoms, an omega-hydroxyalkyl group of 1 to 3 carbon atoms, a group represented by

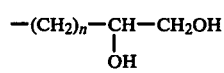

wherein n is 1 to 3, or a carboxyalkyl group of 2 to 4 carbon atoms wherein the hydrogen atom of the carboxyl group may be substituted by an alkaline metal or an atomic equivalent of alkali earth metal.

The above-mentioned ionic chitin derivative, for instance, includes carboxymethylchitin, carboxymethylchitosan, ethylchitosan, glycol chitosan, glyceride chitosan, N-monoethylglycol chitosan, N-monoethylcarboxymethylchitosan, N-propylcarboxymethylchitosan, N-propyllauryl-carboxyethylchitosan, etc. and is cross-linked at the 3 and 6' positions or 3, N and 6' positions.

The above-mentioned cross-linking is further described as follows: the cross-linking at the 3 and 6' positions is denoted a Type I, and the cross-linking at the 3, N and 6' positions is denoted as Type II, shown by the following structures:

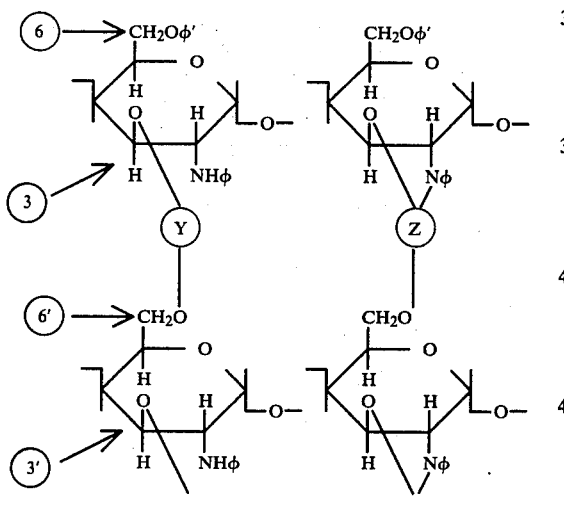

Type I  Type II wherein Y and Z are cross-linking agents, respectively and $\phi$ and $\phi'$ are the functional groups, respectively.

The type of cross-linking is determined by the kind of the cross-linking agent, Y or Z used. In the present invention, either of the two types may be used. The degree of cross-linking is not specifically restricted, however, it is usually 0.01 to 0.3 per pyranose unit.

The cross-linked product of Type I is obtainable, for instance, by the following method of production:

As a raw material, chitin shown by the following formula is used.

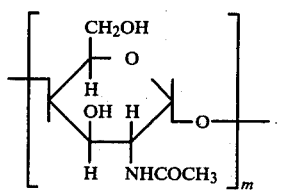

After pulverizing the chitin is used into a suitable size (when regenerated chitin, the shape may be optionally predetermined), the particles of chitin are immersed in an aqueous alkaline solution of high alkali concentration to swell the intermicellular space. An aqueous alkaline solution, at a normality of 10 to 15 of sodium-, potassium- or lithium hydroxide, is used in an amount 3 to 10 times, preferably 3 to 5 times by weight of the raw material of chitin at a temperature of immersion of 5° to 20° C.

Then, in order to make the cross-linking of the chitin easier, the alkali-immersed chitin is subjected to compression or freezing to remove the excess amount of the aqueous alkaline solution. Particularly, the freeze-treatment is preferred in preparation for cross-linking because the chitin micelles are opened by the freeze-treatment and alkali is retained only in the minute interspace between chitin molecules. The freeze-treatment is carried out, depending on the degree of opening of the chitin micelle, at a temperature of −3° to −30° C., preferably −10° to −20° C. for a time period of 3 to 24 hours.

The cross-linking reaction is carried out by adding a cross-linking agent represented by the general formulas of (II) to (V):

 (II)

 (III)

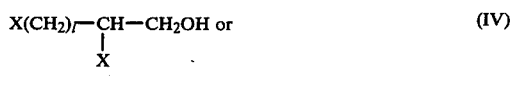 (IV)

 (V)

wherein X denotes a halogen atom and l is an integer of 1, 2 or 3, in an amount 0.1 to 3 times by weight of the original raw material of the chitin (preferably 0.5 to 2 times), to the chitin dealkalized by freeze-treatment or compression, at a temperature lower than the room temperature, preferably at a subzero temperature and by holding at that temperature for 5 to 48 hours.

An example of the cross-linked state of the cross-linked chitin obtainable by the above-mentioned reaction is shown below by a general formula (VI):

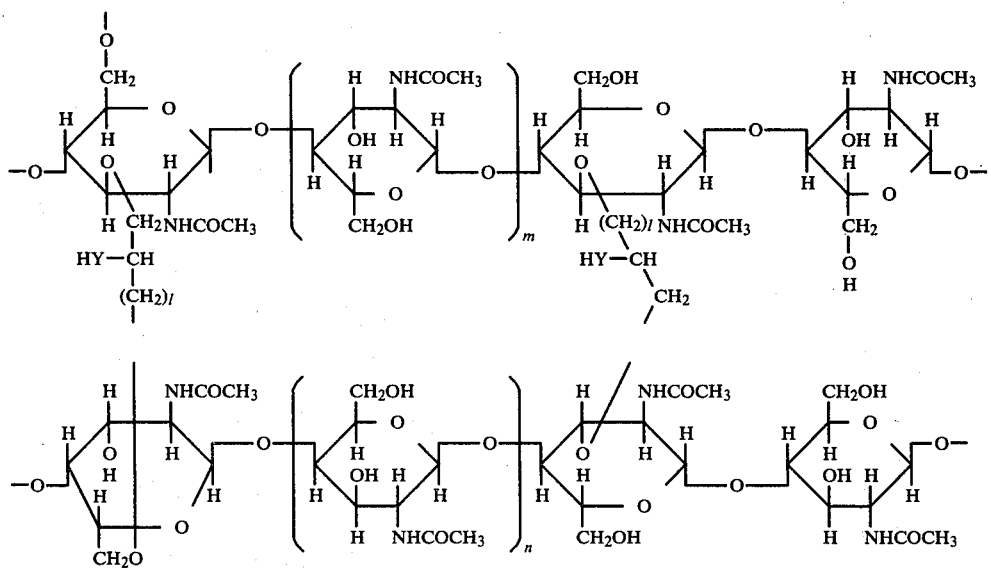

(IV)

wherein l, m and n are an integer and Y is oxygen atom or sulfur atom.

As is clearly seen in the above-mentioned structural formula (VI), the cross-linking is carried out via hydroxyl group(s) or hydroxymethyl group(s) in the same manner as in the carboxyalkylation, etc. shown later. Accordingly, the degree of cross-linking is determined by the degree of substitution by carboxyalkyl group, and in the present invention, the degree of cross-linking is, as has been stated, 0.01 to 0.3 per one unit of N-acetyl-D-glucosamine, the degree of cross-linking being obtained from the elementary analytical data of the cross-linked product.

The cross-linking agent represented by the general formulae (II) to (V) include epichlorohydrin, 1-bromo-3,4-epoxybutane, 1-bromo-4,5-epoxypentane, 1-chloro-2,3-epithiopropane, 1-bromo-2,3-epithiopropane, 1-bromo-3,4-epithiobutane, 1-bromo-4,5-epithiopentane, 2,3-dibromopropanol, 2,4-dibromo-butanol, 2,5-dibromopentanol, 2,3-dibromopropanethiol, 2,4-dibromobutanethiol, 2,5-dibromopentanethiol, etc., and among them, epichlorohydrin, 2,3-dibromopropanol and 1-chloro-2,3-epithiopropane are preferable. In addition, as the cross-linking agent which takes the cross-linked state as Type II, cyanuric chloride and cyanuric bromide are mentioned.

In the next phase, (the introduction of the substituent $R^2$) the derivatives of the above-mentioned cross-linked chitin are obtainable by the following procedures:

The cross-linked chitin is reacted with an amount of the corresponding etherifying agent corresponding to at 0.1 to 0.9, preferably 0.3 to 0.9 per one unit of N-acetyl glucosamin. The mixture is heated in an aqueous alkaline solution of sodium hydroxide or potassium hydroxide. For example, cross-linked carboxyalkylchitin is available by the following procedure:

The alkali-containing cross-linked chitin described above is dispersed into an organic solvent containing an etherifying agent and brought into reaction with the agent at a temperature of 0° to 30° C. for 1 to 72 hours, preferably 5 to 12 hours. In this case, because of the evolution of heat due to neutralization, the temperature is preferably kept at first at 0° to 10° C. and then the reaction is carried out at the predetermined temperature. After the reaction is over, the solvent is distilled off and the residue is dispersed into water. The dispersion is neutralized and filtered to collect the reaction product. The product was de-salted and dried to obtain cross-linked carboxyalkylchitin. The organic solvent used in the carboxyalkylation of the present invention is selected from the group consisting of methanol, ethanol, propyl alcohol, isopropyl alcohol, acetone and dimethylformamide.

The etherifying agent used in the above-mentioned carboxyalkylation is a compound represented by the general formula:

$$X(CH_2)_n-COOH$$

wherein X denotes an atom of chlorine or bromine and n is an integer of 1, 2 or 3. Examples chloroacetic acid, monobromoacetic acid, beta-monochloropropionic acid, beta-monobromopropionic acid, gamma-monochlorobutyric acid, gamma-monobromobutyric acid, etc. used in the amount 1 to 3 times by molecular weight of the raw chitin.

By the above-mentioned method of the present invention, water-insoluble derivative of chitin such as cross-linked carboxymethylchitin, cross-linked carboxyethylchitin and cross-linked carboxypropylchitin are obtained with the degree of carboxyalkylation of generally of 0.1 to 0.9, preferably 0.3 to 0.9. The degree of carboxyalkylation in the present invention is obtained by the elementary analytical data of the product and the titer of an aqueous hydrochloric solution of a specified normality when the product is titrated after converting to its salt at pK value of 4.3.

The shaped material according to the present invention is derived from a de-acetylated product of the cross-linked carboxyalkylchitin, which is obtainable by treating the cross-linked carboxyalkylchitin with an aqueous alkaline solution containing alkali in a high concentration, preferably of a normality of 4 to 15 at 65° to 150° C., preferably 65° to 110° C. for 0.1 to 48 hours to effect de-acetylation.

The cross-linked carboxyalkylchitin used as the starting material of the above-mentioned de-acetylation may be the solvent-including product of the carboxyalkylation in an organic solvent obtained by filtering and washing with ethanol and acetone, the dried product or the product containing water. When the cross-linked carboxyalkylchitin contains water, the normality of alkali in the reaction of the de-acetylation should be corrected to achieve the above-mentioned range. When the reaction temperature of the de-acetylation is lower than the designated one, the reaction takes much more time for completion. On the other hand, the use of higher temperature is not preferable because molecular weight of the product is reduced.

In addition, since the carboxyalkyl group is bonded via the ether linkage, it is not removed in the de-acetylation even when heated in the aqueous alkaline solution.

The degree of de-acetylation in the de-acetylated product is obtained by the elementary analytical data of the product and is 0.1 to 1, preferably 0.3 to 1.

According to the present invention, the deionization of the surface of the cross-linked substance of ionic chitin derivative represented by the formula (I) is carried out in a extremely simple manner. The gelatinized substance of the ionic cross-linked derivative merely is brought into contact with a solution of an organic acid anhydride or a mixture of the anhydride and the organic acid or with a vapour of the anhydride. The deionization thus is carried out by acylation in a very short time period to obtain the shaped material of the invention. The mechanism of the above-mentioned reaction of the deionization has not yet been elucidated, however, the reaction occurs instantaneously on the surface of the gelatinous substance of the formula (I) after the contact with the organic acid anhydride.

The reaction product of the deionization includes a chitin, an N-acylated carboxyalkylchitosan of the formula (VII), a de-carboxyalkylated and N-acylated chitosan of the formula (VIII) and a N-,O-acylated chitosan of the formula (IX):

  (VII)

  (VIII)

  (IX)

wherein R represents $-(CH_3)_m CH_3$ and m is an integer of 0 to 20.

However, the proportion of structural units represented by the general formula (VII) occupying the surface of the shaped material according to the invention is almost zero. Instead, structural units represented by the general formulae (VIII) and (IX), particularly those represented by the formula (IX) occupy the larger part of the surface.

On the other hand, in the inner part of the above-mentioned shaped material, of course depending on the degree of the deionization by acylation, unreacted ionic cross-linked derivative of chitin or its salt remains as the structural units.

Thus, the shaped material according to the present invention is the product in which the surface of the cross-linked substance of the ionic derivative of chitin has been treated by acylation.

The organic acid and acid anhydrides are preferably acetic acid, propionic acid, butyric acid and valeric acid, and their acid anhydrides. However, the carbon chain of the above-mentioned organic acid may be still longer up to 21 carbon atoms. These acids and acid anhydrides may be used alone or mixed with other members, either dilution or after diluted with an organic solvent which does not react with the organic acid or its anhydride. The temperature of acylation is 5° to 80° C., preferably 5° to 60° C., and in the case wherein the organic acid anhydride is used as a gas, the temperature may be still higher than that above-mentioned.

In the contact of the gelatinous of the ionic cross-linked derivative of chitin and the organic acid anhydride, a suitably selected shape may be used according to the desired intended usage of the shaped material of the present invention.

For instance, as one of the shapes, spherical particles of the gelatinous material, which contains water, are dispersed under agitation into the organic acid anhydride. In this state, acylation occurs instantly on the surface of the particles to form a membrane consisted of acylated product. When the reaction is made to proceed further, the organic acid anhydride diffuses into the inner part of the particle and forms the deionized layer of the desired thickness. After making the reaction to proceed for the predetermined time period, the product is separated from the reaction mixture, and washed with water to remove the unreacted organic acid anhydride. Spherical bodies of the shaped material of the present invention are obtained. The thickness and packing density of the acylated membrane is controllable by changing the concentration and amount of the acylating agent, the reaction period and the reaction temperature. Usually the thickness is 0.1 to 1,000 microns and the packing density corresponds to the limit of the molecular weight of 500 to 400,000 of molecules passable through the membrane.

When the ionic cross-linked derivative of chitin is cationic or amphoteric, the shaped material of the present invention is obtained by treating with, as shown above, an acylating agent. On the other hand, when the ionic cross-linked derivative of chitin is anionic, the shaped material of the present invention is obtained by treating with an aqueous dilute acidic solution, such as hydrochloric acid, sulfuric acid, etc. By the acid-treatment, the anionic carboxyalkyl group of the carboxyalkyl derivative is eliminated due to hydrolysis. Of course, the acidic treatment may also be carried out with using the above-mentioned acylating agent as the agent.

The product of the present invention may take any shape according to the corresponding shape of the gelatinous substance of the formula (I), such as the spherical, fibrous, film-like shape a hollow shape of the preceding material as disclosed in the Japanese Patent Application No. 161389/78.

In addition, since the shaped material of the present invention is made up of the cross-linked product of the ionic derivative of chitin and of the acylated product of the cross-linked product, which is permeable to substances and stable chemically and bio-compatibility, the shaped material of the present invention is applicable to a wide range of uses.

One exemplified instance of the above-mentioned uses is the purification and separation of a glycoprotein, of specific size from a mixture of glycoproteins of various molecular weights, wherein only a glycoprotein of molecular weight smaller than a defined value is dispersible into the inner part of the hollow particles of the shaped material of the present invention. Further, the shaped material of the present invention can be used in the form of hollow fibers or film-like shape just as the conventional material for dialysis.

Still more, since proteins are not so much adsorbed on its surface, the shaped material of the present invention can be used as an ion-exchanger while taking advantage of the small reduction of the adsorption velocity in use, the controllability of the permeability to substances and the ionic groups of the shaped material of the present invention. In addition, since the shaped material of the present invention is extremely stable and safe to living bodies, it can be used in the field concerning living bodies, for instance, in blood perfusion, or as an adsorbent for internal administration to adsorb and remove the gastrointestinal toxins or as a covering material of adsorbents and the like.

As has been stated above, the present invention is epochmaking in making chitin utilizable in indefinitely broad field of usage, the utilization of chitin hitherto having been limited to a very narrow field.

The present invention will be explained in more detail while referring to the following non-limitative examples:

EXAMPLE 1

After neutralizing and de-salting by washing with water, the starting material of the present invention, that is, a gel of sodium salt of cross-linked chitin derivative in a shape of spherical particles of 50 to 150 microns in diameter with the degree of cross-linking with epichlorohydrin of 0.1, the degree of carboxymethylation of 0.7 and the degree of deacetylation of 0.9, was separated by filtration, the particles of the gel having been agglomerated by the above-mentioned treatment of de-salting.

Then, 200 g (dried weight: 10 g) of the above-mentioned gel were dispersed into 2 liters of a 1:1 by volume mixture of toluene and acetic anhydride in a flask under agitation to be subjected to the treatment of acylation for 5 min at a room temperature. After the reaction was over, the gel was separated by filtration and washed with ethanol and separately neutralized in another flask containing 2 liters of distilled water.

After neutralization, the product was separated again by filtration, washed with distilled water and subjected to de-salting to obtain the shaped material of the present invention. The size of the spherical particles of the shaped material of the present invention was the same as that of the starting material, however, interparticular agglomeration by de-salting was not recognized. After drying, the shaped material of the present invention showed two infrared absorption peaks, respectively at 1680 and 1500 cm$^{-1}$ and from the fact, the presence of carboxymethyl groups and amino groups was confirmed. Results of the determination and comparison of the capacity of ion-exchange of the shaped material and the starting material of the present invention are shown in Table 1. As is seen in Table 1, the shaped material had the same capacity of ion-exchange as the starting material. When the starting material was treated in an aqueous 2 N hydrochloric acid solution for 5 hours at 50° C., it dissolved completely into the solvent, however, the shaped material treated in the same manner retained its original shape. The insoluble matter to the above-mentioned hydrochloric acid solution was one percent by weight of the dried gel and it was identified as chitin from I.R. spectroscopy and the elementary analysis.

TABLE 1

| | Comparison of Ion-Exchange Capacity | |
|---|---|---|
| Specimen | Cation-Exchange Capacity (meq/g) | Anion-Exchange Capacity (meq/g) |
| Starting material | 3.8 | 5.0 |
| Product of Example 1 | 3.7 | 4.9 |

EXAMPLE 2

Ten grams of the starting material, that is, fibers of cross-linked chitin derivative of 200 microns in diameter with the degree of cross-linking by cyanuric chloride and the degree of deacetylation of 0.9 were made to swell in water. The thus obtained fibrous gel was immersed into one liter of propionic anhydride at 40° C. for 10 min. Then, the thus treated fibers were separated, washed with ethanol and dried.

The starting material and the thus treated fibers were cut into 10 mm in length and respective specimens were treated in 500 ml of an aqueous 2 N hydrochloric acid solution at 50° C. for 5 hours. While the starting material completely dissolved into the solution, the treated fibers left an insoluble substance. After separating the insoluble substance by filtration, it was washed with water and its cross-section was examined under a microscope to find that the insoluble substance was a hollow fiber. From the result, it was considered that the starting material was insolubilized only on its surface.

Since the insoluble substance did not show an infrared absorption at 1500 to 1530 cm$^1$ attributable to amino group, and instead showed infrared absorptions near 1650 and 1550 cm$^{-1}$, respectively, the presence of amide group was presumed and from the elementary analysis, the insoluble substance was identified as N-propionylchitosan.

When the above-mentioned solutions obtained by immersing the starting material and the treated product (with propionic anhydride respectively into the hydrochloric acid solution were respectively neutralized with an aqueous 2 N sodium hydroxide solution, white gel-like substances were obtained, respectively.

After treating these respective gel-like substances by de-salting, they were dried and examined by infrared spectroscopy and elementary analyses. As results, both the two gel-like substances showed an infrared absorption at 1500 to 1530 cm$^{-1}$ attributable to amino group, respectively and after combining their elementary analytical data, they were identified as chitosan, respectively. For confirmation, the above-mentioned hydrochloric acid solutions of the starting material and of the treated product (with propionic anhydride) were brought into reaction with iodine in the presence of sulfuric acid and the purplish coloration was obtained in both solution.

EXAMPLE 3

Each 10 g of spherical particles of cross-linked chitin derivative with the degree of cross-linking with epichlorohydrin of 0.2, the degree of hydroxyethylation of 0.7 and the degree of deacetylation of 0.9, and of gel-like cross-linked chitin derivative with the degree of cross-linking with epichlorohydrin of 0.1, the degree of ethylation of 0.5 and the degree of deacetylation of 0.8 were respectively swollen in water and after removing the excess water, both the swollen gels were respectively dispersed into one liter of a 1:3 by volume mixture of capric anhydride and benzene at 50° C. for 10 min.

Then, both the reaction mixtures were respectively treated in the same manner as in Example 1 to obtain the shaped materials according to the present invention named respectively Shaped materials A and B. That is, Shaped material A was derived from cross-linked de-N-acetylated glycol-chitin and Shaped material B was derived from cross-linked de-N-acetylated ethylchitin. The infrared absorption data and the results of colour reaction of the soluble parts and insoluble parts of the two respective products after treating with an aqueous hydrochloric acid in the same manner as in Example 2 are shown in Table 2. From Table 2, the spherical products were confirmed to have been N-acylated on their surface.

TABLE 2

| | Properties of $HCl_{aq}$-treated substances | | | | | |
|---|---|---|---|---|---|---|
| | Infrared absorption (cm$^{-1}$) | | | | Colour reaction | |
| | 1500 to 1530 | | 1550 | | | |
| Specimen | Insol.[2] | Sol.[1] | Insol. | Sol. | Insol. | Sol. |
| Shaped material A | No[3] | Yes[4] | Yes | No | No | Yes |
| Shaped material B | No | Yes | Yes | No | No | Yes |

Notes:
[1]Sol. means the part of the substance dissolved in the aqueous hydrochloric acid, after recovery from the hydrochloric acid solution.
[2]Insol. means the part of the substance not dissolved in the aqueous hydrochloric acid.
[3]No shows no absorption peak is present.
[4]Yes shows an absorption peak is present.

EXAMPLE 4

Ten grams of the starting material, spherical particles of carboxyethylchitin of the degree of cross-linking by epichlorohydrin of 0.1, the degree of carboxyethylation of 0.5, were swollen with water and after washing the particles with a 1:1 by volume mixture of ethanol and toluene repeatedly to substitute water with the solvent mixture, the solvent mixture in the particles was again substituted with only toluene. The thus toluene-including particles were dispersed into one liter of an aqueous 2 N hydrochloric acid solution under agitation and treated for 15 min at 50° C. After separating the particles by filtration, the particles were put into 100 ml of an aqueous methanolic solution containing 10% by weight of sodium hydroxide (the volume ratio of water/methanol being 1:2). After separating the particles by filtration, the particles were washed with distilled water. The thus treated particles and starting material were respectively added to distilled water in which 10 g of the starting material of Example 3, that is, spherical particles of glycol-chitin had been dispersed, the particles of the starting material of this example were agglomerated, whereas the spherical particles were not aggromerated and it was confirmed that the latter had no ionic properties on its particles' surface.

EXAMPLE 5

The spherical particles obtained in Example 1 were filled in a glass column of 10 mm and 200 mm in diameter and length, respectively. Separately, after dispersing the starting material of Example 1 into an aqueous 2% sodium chloride solution, the particles of the starting material of Example 1 were filled in a column with the same dimensions as mentioned above and distilled water was passed through the thus filled column until no more sodium chloride was detectable in the effluent to obtain the reference column.

Each one milligram of bovine serum fibrinogen (Fraction 1) and bovine serum albumin were dissolved into each 10 ml of distilled water respectively, and the thus prepared two solutions were mixed well to make a combined solution.

After pouring the combined solution into each of the above-mentioned two columns in an amount of each one milliliter, the columns were developed with distilled water at a rate of one milliliter/min.

Whereas, in the effluent of 4 to 5 ml from the column filled with the spherical particles according to the present invention a substance having absorption in ultraviolet region was detected, such a substance was not detected in the effluent from the column filled with the starting material of Example 1. The substance having absorption in ultraviolet region was identified by liquid-chromatography, etc. as fibrinogen.

The same experiments were repeated, however, using an aqueous 0.1 N sodium chloride solution instead of distilled water used in development. In this case, in the 10 to 12 ml of the effluent from the column filled with the spherical particles according to the present invention, albumin was detected as a substance showing an ultraviolet absorption, without accompanying anything. In the effluent from the column filled with the starting material in Example 1, each one compound showing ultraviolet absorption was detected in the fraction of 5 to 7 ml and 10 to 12 ml, respectively, and they were identified as fibrinogen and albumin, respectively.

As is seen above, the shaped material according to the present invention shows an exclusive limit depending upon the molecular weight of protein, and accordingly, the shaped material according to the present invention is usable in fractionation of proteins depending on their molecular weight.

EXAMPLE 6

The present example shows the results of measurement of mechanical strength of the shaped material according to the present invention, prepared in Example 1.

The measurement was carried out as follows:

After filling the shaped material of the present invention in a column of 20 mm and 125 mm, respectively in diameter and height, to the height of 100 mm, distilled water was introduced from the inlet of the column via a pump fitted with a pressure gauge to examine the relationship between the introductory pressure and the rate of effluent of distilled water at the outlet of the column. A comparative measurement was carried out by using de-acetylated product of not-cross-linked carboxymethylchitin as the filling material of the column, the above-mentioned de-acetylated product being prepared as follows:

An aqueous 2% by weight solution of an acetate of deacetylated product of carboxymethylchitin of the degree of carboxymethylation of 0.7 and the degree of deacetylation of 0.9 was added dropwise to a 10:1 by volume mixture of acetic anhydride and acetic acid to bring into reaction under agitation for 5 min at room temperature. After the reaction was over, the reaction mixture was neutralized and the product was separated by filtration and washed with water to obtain the deacetylated product of not-cross-linked carboxymethylchitin.

The results of the mechanical strength test are shown in the attached drawing. As is shown in the drawing, in the case of the comparative specimen, the deformation of the shaped material caused by the increased pressure reduced the rate of flow of distilled water, whereas, in the case of the shaped material according to the present invention, no reduction of the flow rate due to the increased pressure was observed to proof the superior mechanical strength of the shaped material according to the present invention.

What is claimed is:

1. A shaped material of a chitin derivative having a surface layer consisting essentially of chitin derivative obtained by acylation or acid-treatment of a 3,6' or 3,N,6' cross-linked ionic chitin-derivative of which the main structural unit is represented by the formula:

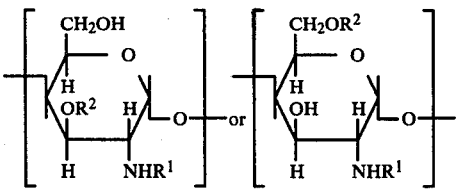

wherein $R^1$ represents a hydrogen atom, $-C_nH_{2n+1}$ or $-(CH_2)_nOH$; $R^2$ represents a hydrogen atom, $-C_{n'}H_{2n'+1}$, $-(CH_2)_nOH$, $-(CH_2)_{n'}CH(OH)CH_2OH$ or $-(CH_2)_{n'}COOM$, wherein n is an integer of 1 to 20, n' is an integer of 1 to 3 and M represents a hydrogen atom, an alkali metal atom or an atomic equivalent amount of an alkaline earth metal, or a de-N-acylated acyl chitin having an acyl group of $-CO(CH_2)_{n-1}CH_3$ and which is cross-linked at a rate of 0.01 to 0.3 per pyranose ring.

2. The shaped material of claim 1 wherein the ionic chitin derivative is cross-linked between the positions of 3 and 6' or the positions of 3, nitrogen at position 2 and position 6'.

3. The shaped material of claim 1 wherein said surface is at least one derivative selected from the group consisting of chitin, O-acylated chitin, N-acylated chitosan and o-, N-diacylated chitosan.

* * * * *